United States Patent
Donovan

(10) Patent No.: US 7,485,624 B2
(45) Date of Patent: *Feb. 3, 2009

(54) METHOD FOR TREATING CARDIAC MUSCLE DISORDERS

(75) Inventor: Stephen Donovan, Capistrano Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/236,478

(22) Filed: Sep. 26, 2005

(65) Prior Publication Data

US 2006/0083757 A1    Apr. 20, 2006

Related U.S. Application Data

(63) Continuation of application No. 09/371,354, filed on Aug. 10, 1999, now Pat. No. 6,977,080.

(51) Int. Cl.
*A61K 38/16* (2006.01)
*C07K 14/33* (2006.01)

(52) U.S. Cl. ........................... 514/12; 530/825
(58) Field of Classification Search ............... 514/12; 530/825
See application file for complete search history.

(56) References Cited

U.S. PATENT DOCUMENTS

| | | | |
|---|---|---|---|
| 4,920,116 A * | 4/1990 | Morgan, Jr. et al. ..... | 514/210.01 |
| 5,766,605 A | 6/1998 | Sanders et al. | |
| 5,865,794 A | 2/1999 | Castro | |
| 6,623,742 B2 | 9/2003 | Voet | |
| 6,767,544 B2 * | 7/2004 | Brooks et al. ............ | 424/247.1 |
| 6,869,610 B2 | 3/2005 | Aoki et al. | |

FOREIGN PATENT DOCUMENTS

WO    WO 9517904 A2 *    7/1995

OTHER PUBLICATIONS

Lamanna et al., "Cardiac effects of botulinal toxin," Arch Int Pharmacodyn 293:69-83, 1988.*
Waxman et al., "Persistent primary coronary dilation induced by transatrial delivery of nitroglycerin into the pericardial space: a novel approach for local cardiac drug delivery," J Am Coll Cardiol 33(7):2073-2077, 1999.*
KSR international Co. v. Teleflex Inc. et al., 550 US __(2007), Apr. 30, 2007.*
Sauviat, M.-P., "Modulation muscarinique de l'activite cardiaque," J Soc Biol 193(5):469-480, 1999.*
Dickson, E., *Studies on the Manner in which the Toxin of Clostridium Botulinum Acts Upon the Body*, J. Exper Med 37: 711-31 (1923) d.
Braunwald, E., *Heart Disease A Textbook of Cardiovascular Medicine*, fifth edition (1997), two volumes, W.B. Saunders Company.
Opie, L., *Drugs for the Heart*, fourth edition (1997), W.B. Saunders Company.
Fauci, A., *Harrison's Principles of Internal Medicine* fourteenth edition (1997), McGraw Hill.
Nattel, S., *Comparative Mechanisms of Acton on Antiarrhythmic Drugs*, Am J. Cardiol, 72: 13F-17F (1993).
Wit, A., *Electrophysiological Basis for Antiarrhythmic Drug Action*, Clin. Physiol. Biochem. 3: 127-134 (1985).
Waxman, S., *Persistent Primary Coronary Dilation Induced by Transatrial Delivery of Nitroglycerin into the Pericardial Space: A Novel Approach for Local Cardiac Drug Delivery*, J Am Coll Cardiol 33: (7); 2073-2077 (1999).
Claus, D., *Botulinum Toxin: Influence on Respiratory Heart rate Variation*, Mov Disord 10(5): 574-9 (1995).
Kimura, K., *Negative Chronotropic Effect of Botulinum Toxin on Neonatal Rat Cardiac Myocytes*, Biochem Biophys Res Commun 6; 244 91): 275-9 (1998).
Nebe, A., *No Effects on Heart-Rate Variability and Cardiovascular Reflex Tests After Botulinum Toxin Treatment of Cervical Dystonia*, Mov Disord; 11 (3): 337-9 (1996).
Glaradi, G., *The Local Injection of Botulinum Toxin can Affect the Neural Control of Heart Rate Variability*, Neural 44; (Sup 2): A307-A308 (1994).
Laham, R., *Therapeutic Myocardial Angiogenesis Using Percutaneous Intrapericardial Drug Delivery*, Clin Cardiol; 22 (supp 1): 16-19 (1999).
Laham, R., *Subxyphoid Access of the Normal pericardium: A Novel Drug Delivery Technique*, Cath & Cardiovasc Inter 47:109-111 (1999).
Sonobe, T., *Development of Intracoronary Local Adhesive delivery Technique*, Int. J Artic Organs 20(6); 319-326 (1997).
Avitall, B., *Iontophoretic Transmyocardial Drug Delivery. A Novel Approach to Antiarrhythmic Drug Therapy*, Circulation 85: 1582-93 (1992).

(Continued)

*Primary Examiner*—Jon P Weber
*Assistant Examiner*—Rosanne Kosson
(74) *Attorney, Agent, or Firm*—Claude L. Nassif; Stephen Donovan; Martin Voet

(57) ABSTRACT

Methods for treating cardiac muscle disorders, such as cardiac arrhythmias, by administration of a neurotoxin to cardiac muscle are disclosed. Bradycardia can be alleviated for several months by a single intrapericardial or intracardiac injection or infusion of a botulinum toxin. Tachycardia can be alleviated by preganglionic sympathetic nervous system administration of a botulinum toxin.

18 Claims, No Drawings

OTHER PUBLICATIONS

Ayer GM, *Amiodarone Instilled into the Canine Pericardial Sac Migrates Transmurally to Produce Electrophysiologic Effects and Suppress Atrial Fibrillation* J Cardiovasc Electrophysiol 7: 713-21 (1996).

Labhasetwar V., *Epicardial Administration of Ibutilide from Polyurethane Matrices: Effects on Defibrillation Threshold and Electrophysiologic Parameters* J Cardiovasc Pharmacol 24: 826-40 (1994).

Lambert, C., *Local Drug Delivery*, Cath & Cardiovasc Diagn 41: 231 (1997).

Glazier, J., *Site-Specific Intracoronary Thrombolysis With Urokinase-Coated Hydrogel Balloons: Acute and Follow-Up Studies in 95 Patients*, Cath & Cardiovasc Diagn 41: 246-253 (1997).

Bartorelli, A., *Local Heparin Delivery Prior to Coronary Stent Implantation: Acute and Six Month Clinical And Angiographic Results*, Cath & Cardiovasc Diagn 42: 313-320 (1997).

Nebe, A., *Influence of Botulinum Toxin Type A on the Heart Rate Variability in Patients with Cervical Dystonia*, Mov Dis 10; 3: 389 (1995).

Claus, D., *Distant Effects of Botulinum Toxin on Autonomic Cardiac Reflexes*, Mov Dis 10: 3: 389 (1995).

Thomas, C., *Local Intracoronary Heparin Delivery With a Microporous Balloon Catheter*, Amer Heart J 132; 5: 969-972 (1996).

Camemzind, E., *Site-Specific Intravascular Administration of drugs: History of a Method Applicable in Humans*, Cath & Cardiovasc Diagn 41: 342-347 (1997).

Lamanna, C., et al.; Cardiac Effects of Botulinal Toxin; *Arc Int. Pharmacodyn*.; 1988; vol. 293; 69-83.

McDermott, D.A., et al.; Use of an Indwelling Catheter for Examining Cardiovascular Responses to Pericardial Administration of Bradykinin in Rat; *Cardiovascular Research*; 1995; vol. 30; 39-46.

Kimura et al..; "*Negative Chronotropic Effect of Botulinal Toxin on Neonatal Rat Cardiac Mycocytes . . .* " Biochem. Biophys. Res. Comm., vol. 244, 1998, pp. 275-279.

Sauviat M-P.: "Effect of Neurotoxins on the Electrical and Mechanical Activity of Heart Muscle", *Comptes Rendus Des Seances De La Societe De Biolobie Et De Ses Filiales.*, vol. 191, 1997, pp. 451-471.

Johnson, Eric; Clostridial Toxins as Therapeutic Agents; Benefits of Nature's Most Toxic Proteins, *Annu Rev Microbiol* 53: 551-575, 1999.

Schmitt et al.; "Bacterial toxins: friends or foes?" *Emerg Infect Dis* 5(2): 224-234, 1999.

Tsuboi et al.; "Botulinum Neurotoxin A Blocks Cholinergic Ganglionic Neurotransmission in the Dog Heart". Jpn J. Pharmacol 89 (3); 249-254, 2002.

Tsuboi et al.; "Inotropic Chronotropic and Dromotropic Effects Mediated Via Parasympathetic Ganglia in the Dog Heart." *Am J Physiol Heart Circ Physiol* 279: H1201-H1207, 2000.

Mangrum et al., "The Evaluation and Management of Bradycardia". *N Eng J Med* 342(10): 703-709, 2000.

\* cited by examiner

METHOD FOR TREATING CARDIAC MUSCLE DISORDERS

CROSS-REFERENCE TO RELATED APPLICATIONS

This application is a continuation application of U.S. application Ser. No. 09/371,354, filed Aug. 10, 1999, now U.S. Pat. No. 6,977,080, issued Dec. 20, 2005, the entire contents of which are hereby incorporated by reference.

BACKGROUND

The present invention relates to a method for treating cardiac muscle disorders. In particular, the present invention relates to a method for treating cardiac arrhythmia by administration of a neurotoxin to cardiac muscle.

The pumping action of the heart is controlled by sympathetic and parasympathetic (primarily vagal) nerves which abundantly innervate the heart. Heart rate can be increased by sympathetic stimulation and decreased by vagal stimulation. Additionally, many cardiac fibers, such as the sinus node (also called sinoatrial or SA node) have the capability of self-excitation. Stimulation of the sympathetic nerves causes release of norepinephine at the sympathetic nerve endings. Contrarily, stimulation of the parasympathetic nerves to the heart causes acetylcholine to be released at the vagal nerve endings. Hence, the parasympathetic nervous system is often referred to as a cholinergic system.

The release of acetylcholine by the postganglionic parasympathetic nerve endings, by acting upon the muscarinic receptors present in cardiac muscle tissue, as indicated, decreases the rate of rhythm of the sinus node and decreases the excitability of the AV junctional fibers between the atrial musculature and the AV node, thereby slowing transmission of the cardiac impulse into the ventricles. The major site of action of parasympathetic control of the heart appears to be the sinoatrial node, where it reduces the heart rate in contrast to sympathetic stimulation. Other lesser parasympathetic activities include inhibition of the AV node and a mild inhibitory effect on contractile force.

In athletes, parasympathetic activity can increase to slow the heart rate. With excessive physical training, the AV node can be inhibited to block the conduction of the impulse from the SA node to the ventricles, resulting in the condition referred to as AV block.

Notably, all preganglionic neurons are cholinergic in both the sympathetic and parasympathetic nervous systems. Therefore acetylcholine or acetylcholine like substances when applied to the ganglia will excite both sympathetic and parasympathetic postganglionic neurons. Additionally, all or almost all of the postganglionic neurons of the parasympathetic nervous system are also cholinergic. Acetylcholine activates two types of receptors, muscarinic and nicotinic receptors. Parasympathomimetic drugs such as pilocarpine and methacholine mimic the effect of acetylcholine.

Arrhythmia

Cardiac muscle disorders, such as arrhythmias and fibrillations, can result in incapacitation and death. During ventricular fibrillation, the ventricles can quiver in an irregular chaotic way so that little blood is pumped out of the heart and the body, particularly the brain, is deprived of oxygen. During ventricular tachycardia, the heart beats too fast because of rapid electrical impulses starting in the ventricles, which also decreases bloodflow and deprives the body of oxygen.

Natural cardiac rhythms are maintained through the cooperation of sympathetic nerves, which can increase the rate at which the heart beats, and the vagus nerve which can slow down the rate at which the heart beats.

Electrochemical messages from the sympathetic and vagal nerves reach the heart's natural pacemaker, the sinoatrial node, progress to the upper chambers (the atria), and pause at the atrioventricle node, before entering the main pumping chambers, the ventricles. Any breach of this electricalchemical circuit can cause the heart to lurch into a chaotic rhythm.

Arrhythmias are caused by a disruption of the normal functioning of the electrical conduction system of the heart. Normally, the chambers of the heart (atria and ventricles) contract in a coordinated manner. The signal to contract is an electrical impulse that begins in the sinoatrial node (sinus or SA node). This impulse is conducted through the atria and stimulates them to contract. The impulse passes through the atrioventricular node, then travels through the ventricles and stimulates them to contract. Problems can occur anywhere along the conduction system, causing various arrhythmias. Problems can also occur in the heart muscle itself, causing it to respond differently to the signal to contract, also causing arrhythmias, or causing the ventricles to contract independently of the normal conduction system.

Arrhythmias include tachycardias, bradycardias and true arrhythmias of disturbed rhythm. Arrhythmias are classified as lethal if they cause a severe decrease in the pumping function of the heart. When the pumping function is severely decreased for more than a few seconds, blood circulation is essentially stopped, and organ damage (such as brain damage) can occur within a few minutes. Lethal arrhythmias include ventricular fibrillation, also ventricular tachycardia that is rapid and sustained, or pulseless, and may include sustained episodes of other arrhythmias. Additional types of arrhythmias include atrial fibrillation or flutter, multifocal atrial tachycardia, paroxysmal supraventricular tachycardia, Wolff-Parkinson-White syndrome, sinus tachycardia, sinus bradycardia, bradycardia associated with heart block, sick sinus syndrome, and ectopic heartbeat.

In sinus arrhythmia there are cyclic changes in the heart rate during breathing. In sinus tachycardia the sinus node sends out electrical signals faster than usual, speeding up the heart rate. In sick sinus syndrome the sinus node does not fire its signals properly, so that the heart rate slows down. Sometimes the rate changes back and forth between a slow (bradycardia) and fast (tachycardia) rate. With premature supraventricular contractions or premature atrial contractions (PAC) a heart beat occurs early in the atria, causing the heart to beat before the next regular heartbeat. In supraventricular tachycardia (SVT) and paroxysmal atrial tachycardia (PAT) a series of early beats in the atria speed up the heart rate (the number of times a heart beats per minute). In paroxysmal tachycardia repeated periods of very fast heartbeats begin and end suddenly. In atrial flutter there are rapidly fired signals which cause the heart muscles in the atria to contract quickly, leading to a very fast, steady heartbeat. In atrial fibrillation electrical signals in the atria are fired in a very fast and uncontrolled manner. The electrical signals arrive in the ventricles in a completely irregular fashion, so the heart beat is completely irregular. In the Wolff-Parkinson-White syndrome, abnormal pathways between the atria and ventricles cause the electrical signal to arrive at the ventricles too soon and to be transmitted back into the atria. Thus very fast heart rates may develop as the electrical signal ricochets between the atria and ventricles.

Arrhythmias which originate in the ventricles include premature ventricular complexes (PVC) in which an electrical signal from the ventricles causes an early heart beat that generally goes unnoticed. The heart then seems to pause until the next beat of the ventricle occurs in a regular fashion. In ventricular tachycardia the heart beats fast due to electrical signals arising from the ventricles (rather than from theatria). In ventricular fibrillation electrical signals in the ventricles are fired in a very fast and uncontrolled manner, causing the heart to quiver rather than beat and pump blood.

It is known that some arrhythmias are also caused by some drugs. These include antiarrhythmics, Beta blockers, caffeine, cocaine, psychotropics, and sympathomimetics.

Tests that reveal arrhythmias, and which can differentiate between the different types of arrhythmia, include echocardiogram (ECG or EKG), coronary angiography and electrophysiologic study (EPS), the later requiring cardiac catheterization. An ECG records the changing potentials of the electrical field imparted by the heart. Echocardiography refers to a group of tests that utilize ultrasound to examine the heart and record information in the form of reflected sonic waves. Magnetic resonance imaging can also be used as a noninvasive means to determine, at least to some extent, intracardiac pressures and cardiac anatomy. Further details regarding theses diagnostic procedures can be found in *Heart Disease A Textbook of Cardiovascular Medicine*, edited by Eugene Braunwald, (1997), two volumes, fifth edition, published by W.B. Saunders Company, the entire contents of which is incorporated herein by reference in its entirety.

Therapy for arrhythmia can include systemic administration (by oral or intravenous routes) of an antiarrhythmic drug, surgical removal of the arrhythmic tissue, and/or or implantation of a defibrillator or pacemaker Drug Therapy for Arrhythmia The traditional treatment for the erratic heartbeat of arrhythmia is oral or intravenous administration of an antiarrhythmic drug. A wide variety of antiarrhythmic drugs, such as amiodarone and sotalol, are known, as set forth in *Drugs for the Heart* by Lionel H. Opie (1997) published by W.B. Saunders Company, the entire contents of which are incorporated herein by reference in its entirety. Antiarrhythmic drugs are generally classified based on their major effects on the heart. Category IA drugs include quinidine, procainamide and disopyramide. Category IB drugs include lidocaine, mexiletine. Category IC drugs include flecainide and propafenone. Category II drugs include beta-blocking drugs. Category III drugs include amiodarone, ibutilide and sotalol. Category IV drugs include calcium-blocking drugs. The category IA, IC and III antiarrhythmic drugs have the major side effects of torsades de points and sudden death. See e.g. Chapter 7. "Antiarrhythmic Drugs" in *Drugs for the Heart*, supra and Nattel, S., *Comparative Mechanisms of Action of Antiarrhythmic Drugs*, Am J. Cardiol, 72: 13F-17F (1993), and Wit, A., *Electrophysiological Basis for Antiarrhythmic Drug Action*, Clin. Physiol. Biochem. 3: 127-134 (1985), both of which later two publications are incorporated herein in their entireties Certain arrhythmias, such as atrial fibrillation, can occur post-operatively and various drugs have been administered both pre-operatively and re-initiated immediately after surgery as an intravenous medication to try and treat this condition. Unfortunately, drugs such as sotalol administered intravenously to treat post-operative atrial fibrillation can cause ventricular pro-arrhythmia. Additionally, conditions such as obstructive lung disease and congestive heart failure limit the use of beta blockers antiarrhythmic drugs such as sotalol.

A significant problem with the use of most if not all antiarrhythmic drugs occurs because antiarrhythmic drugs are typically administered intravenously or intraperitoneally resulting in rapid metabolic clearance rates, with concomitant short duration of effective drug level and low drug efficiency. Furthermore, a number of the antiarrhythmic drugs can also have proarrhythmic effects upon the heart.

Thus, current drug therapy for arrhythmia whether by oral or parenteral administration into the systemic circulation has many drawbacks and deficiencies, including undesired and deleterious systemic side effects (lack of selectivity), short duration of action and substantial antigenicity (drug resistance). Additionally, the antiarrhythmic drugs used are expensive, require the person being treated to remember to take them on at least a daily basis, can render the patient groggy and lethargic. and are contraindicated for certain patients.

Bradycardia

Significantly, almost one half of all unexpected cardiac arrests which result in sudden death are caused by bradyarrhythmia. Bradyarrhythmia or synonymously bradycardia can be defined as any disturbance of the heart's rhythm which results in a heart rate of under sixty beats per minute. Bradyarrhythmia may occur without obvious underlying cause and without the existence of a previous event such as a myocardial infarction or pulmonary embolism.

Tragically, it is known that sudden death in heart failure resulting from acute myocardial ischemia or infarction, pulmonary embolism, embolic or hemorrhagic stroke, hyperalemia as well as conduction system disease can all be caused by a prior bradycardiac episode.

Drugs that block the effect of acetylcholine, and hence the inhibitory effect of the vagal nerve on the heart, upon the muscarinic type of cholinergic effector organs include atropine and similar drugs such as homatropine and scopolamine. These drugs do not affect the nicotinic receptor action of acetylcholine on the postganglionic neurons or on skeletal muscle. Atropine has a vagolytic effect that is useful for the management of bradyarrhythmias with atrioventricular (AV) block, particularly with inferior infarction, sinus or nodal bradycardia with hypotension, or bradycardia-related ventricular ectopy. Small doses and careful monitoring are essential since the elimination of vagal inhibition may unmask latent sympathetic overactivity, thereby producing tachycardia.

Unfortunately, while symptomatic sinus bradycardia, sick sinus syndrome and sinoatrial disease can be treated with probanthine or by chronic administration of atropine, the results are unsatisfactory in the long run so that implantation of a cardiac pacemaker is the typical therapeutic choice for chronic bradycardia. Additionally, for AV block with syncope or with excessively slow heart rates, atropine or isoproterenol or transthoracic pacing has been used as an emergency measure, but again, only pending pacemaker implantation. Thus, many drawbacks and deficiencies exist with current therapy for bradycardia.

Surgical Removal of Arrhythmic Tissue

Surgery can be carried out to excise the cardiac tissue causing an arrhythmia where the arrhythmia is unresponsive to antiarrhythmic drug therapy. Although closed approaches, such as by biotome catheterization have been used for some of cardiac surgery such as for example, to remove myxomas, including atrial myxomas, closed approach surgical treatment of arrhythmic cardiac tissue is typically treated by either catheter mediated cryoablation or by radiofrequency ablation. Radiofrequency ablation has been used to treat tachycardias such as supraventricular tachycardias and some ventricular tachycardias.

In radiofrequency ablation a catheter enclosing conductive wires with terminal electrodes near the open end or tip of the catheter is inserted into a patient's body through a vein in the thigh, shoulder, or neck. Upon being threaded intravenously to the heart, the catheter tip is positioned inside the heart next to the abnormal heart tissue that is responsible for the tachycardia. Then, a small amount (about 50 watts) of energy is applied to the heart between the tip electrode and a skin patch that is usually placed behind the left shoulder. This energy heats up and thus dries out the heart tissue that is within about 5 millimeters of the tip. After about 30 to 60 seconds of heating, this tissue is no longer alive and can no longer cause tachycardia. Although the actual ablation takes only a minute, the procedure often takes 4 to 10 hours. The reason being that it is time-consuming to identify the exact tissue in the heart that is responsible for a tachycardia and to make sure that all of the relevant tissue has been ablated completely.

Cardiac arrhythmias treatable by radiofrequency ablation include atrioventricular nodal reentrant tachycardia (AVNRT), atrioventricular tachycardia (AVRT) that uses an accessory bypass tract for retrograde conduction, atrial tachycardias that occur in otherwise-normal hearts and also in hearts that have had prior surgery, atrial flutter, and some kinds of ventricular tachycardia that occur in otherwise-normal hearts. The first three rhythms are often grouped together with the term "supraventricular tachycardia", although this term can also be used to include atrial flutter and atrial fibrillation.

Subsequent to radiofrequency, a cardioverter-defibrillator is often implanted in the patient to prevent recurrence of subsequent arrhythmia by non-ablated cardiac tissues.

Unfortunately, while radiofrequency ablation can treat, it usually does not cure supraventricular tachycardias, including atrial flutter and atrial fibrillation. When a tachycardia is not controlled by antiarrhythmic drugs and cannot be cured by ablation, the symptoms of the arrhythmia (but not the arrhythmia itself) can often be controlled by either intentional destruction of the AV node itself or by ablation of the slow AV nodal pathway. In intentional destruction of the AV node, by AV junctional ablation, the upper and lower chambers of the heart are electrically disconnected and the procedure mandates immediate implantation of a permanent pacemaker. AV nodal ablation is used to control otherwise unresponsive atrial fibrillation.

Ablation of the slow AV nodal pathway is the same procedure used to treat AV nodal reentrant tachycardia. For uncontrollable atrial fibrillation and other supraventricular tachycardias, this procedure offers some of the benefit of AV junctional ablation without the need for implantation of a permanent pacemaker. The slow AV nodal pathway procedure takes advantage of the fact that the heart in most patients has two parts to the AV node. The "fast" AV nodal pathway conducts rapidly but takes a long time to recover enough to conduct the next heart beat. The "slow" AV nodal pathway is a backup pathway that conducts slowly but can recover very quickly. At most heart rates, patients use only the fast pathway. When the heart is beating very rapidly (during vigorous exercise, for example), the slow pathway is used because the fast pathway can't recover fast enough between heart beats. When the slow pathway is removed by ablation, the patient almost never can tell the difference at usual heart rates (even during vigorous exercise to, say, a heart rate of 180-200 beats per minute). If a very rapid heart rate (say, to 250 bpm) occurs in the atria, however, the ventricles will go more slowly than they would with an intact slow pathway.

In older patients, who are the ones who usually develop sustained atrial fibrillation, the fast pathway does not conduct as rapidly as in young people, so the maximum heart rate can often be reduced to a range that is tolerable. Two problems with the slow AV nodal procedure for atria fibrillation are, first, when the procedure is continued until the heart rate in atrial fibrillation is reasonable (say, 130 bpm during infusion of isoproterenol, which speeds up the heart rate), about 20% of patients get complete heart block and require immediate implantation of a permanent pacemaker. Second, patients who have undergone the slow AV nodal procedure often don't feel as well as those who go ahead and have AV junctional ablation and pacemaker insertion. The reason seems to be that the heart rate is still erratic because the ventricular rhythm still follows the irregularly atrial fibrillation. By contrast, patients who have AV junctional ablation and pacemakers have regular rhythms because the pacemakers set the heart rate for them.

Unfortunately, the radiation used during the ablation procedure can potentially cause cancer, especially breast cancer in women.

Hyperlipidemia doesn't affect the supraventricular rhythms that are the usual targets of ablation. When ablation is used for the type of ventricular tachycardia that occurs in people who have had myocardial infarction, however, control of hyperlipidemia is quite important to prevent recurrent infarction.

Finally, arrhythmia can also be treated by implantation of a cardiac defibrillator or by implantation of an artificial pacemaker. A cardiac defibrillator is surgically implanted beneath the skin of a patient's abdomen and connected by wires to the ventricles. When arrhythmia occurs, the defibrillator sends an electrical charge to the heart in an attempt to restore normal heartbeat. A defibrillator does not prevent the onset of arrhythmia, but merely attempts to restore the heart's normal rhythm by providing an electric shock to the heart to disrupt an ongoing arrhythmia. Importantly, both defibrillators and pacemakers can malfunction and misfire due, for example, to the effect of proximity to an airport metal detector or store security check out device. Furthermore, significant drawback to the use of both defibrillators and pacemakers include the requirement for surgery to implant with attendant risks such as infection.

Angina

A commonly prescribed drug for angina is nitroglycerin, which relieves pain by widening blood vessels. More blood can thereby flow to the heart muscle and the work load of the heart is decreased. Nitroglycerin can be administered when discomfort occurs or is expected. Other drugs to treat angina include beta blockers to slow the heart rate and lessen the force of the heart muscle contraction and calcium channel blockers for reducing the frequency and severity of angina attacks.

Botulinum Toxin

The anaerobic, gram positive bacterium *Clostridium botulinum* produces a potent neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture. The botulinum toxin passes unattenuated through the lining of the gut and attacks the central nervous system. The highest cranial nerves are affected first, causing medial rectus paresis, ptosis, and sluggish pupillary response to light. Subsequent symptoms of botulinum toxin poisoning include difficulty walking, swallowing, and speaking to paralysis of the respiratory muscles, resulting in suffocation and death.

Botulinum toxin is the most lethal natural biological agent known to man. It has been determined that 39 units per kilogram of intramuscular BOTOX® is a $LD_{50}$ in primates. One unit (U) of botulinum toxin can be defined as the $LD_{50}$ upon intraperitoneal injection into mice. BOTOX® contains 4.8 ng of botulinum toxin type A per 100 unit vial. Thus, for a 70 kg human a $LD_{50}$ of 39 U/kg would be about 131 ng or 27.3 vials (2730 units) of intramuscular BOTOX®. Seven immunologically distinct botulinum toxins have been characterized, being respectively botulinum toxin serotypes A, B, C1, D, E, F and G each of which is distinguished by neutralization with type-specific antibodies. The neurotoxin component is non-covalently bound to nontoxic proteins to form high molecular weight toxin complexes. The different serotypes of botulinum toxin vary in the animal species that they affect and in the severity and duration of the paralysis they evoke. Botulinum toxin type A is the most potent of the seven known serotypes produced by the *Clostridium botulinum* bacteria and has, in minute quantities, become an important pharmaceutical for the treatment of various segmental and peripheral movement disorders associated with muscle overactivity, such as spasticity, as well as pain, and various other neuronal disorders.

At a normal neuromuscular junction, a nerve impulse triggers the release of acetylcholine, which causes the muscle to contract. Hyperactive muscle contraction is characterized by excessive release of acetylcholine at the neuromuscular junction. The use of a botulinum toxin can be effective in reducing the excessive activity by blocking the release of acetylcholine at the neuromuscular junction.

Botulinum toxin is known to act to reduce excess muscle (both skeletal and smooth muscle) and sphincter contraction and to reduce certain glandular activities upon direct injection into the hyperactive or hypertonic muscle or gland and is believed to exert its effect by entering peripheral nerve terminals at the neuromuscular junction and by blocking the release of acetylcholine. Affected terminals are inhibited from stimulating muscle contraction or inducing glandular activity, resulting in a reduction of muscle tone or reduce secretory output by the targeted gland. Thus, when injected intramuscularly at therapeutic doses, botulinum toxin produces a localized chemical denervation and hence a localized weakening or paralysis and relief from excessive involuntary muscle contractions. When the muscle is chemically denervated, it atrophies and may then in response develop extrajunctional acetylcholine receptors.

Clinical effects of peripheral intramuscular botulinum toxin are usually seen within one week of injection. The typical duration of symptomatic relief from a single intramuscular injection average about three months or longer. Muscles therapeutically treated with a botulinum toxin eventually recover from the temporary paralysis induced by the toxin, due possibly to the development of new nerve sprouts or to reoccurrence of neurotransmission form the original synapse, or both. A nerve sprout establishes a new neuromuscular junction. Thus, neuromuscular transmission can gradually return to normal over a period of several months with no lasting side effects.

Botulinum toxin has no appreciable affinity for organs or tissues other than cholinergic neurons and when it does bind to neuronal receptors, its only known action is to block acetylcholine release without causing neuronal cell death. Botulinum toxin has therefore been used to treat a variety of disorders of cholinergic nervous system transmission.

Botulinum toxins have been used for the treatment of an increasing array of neurologic disorders, most of which are characterized by hyperactive neuromuscular activity in specific focal or segmental muscle regions. Thus intramuscular or intraglandular injection of one or more of the botulinum toxin serotypes has been used to treat, blepharospasm, spasmodic torticollis, hemifacial spasm, spasmodic dysphonia, oral mandibular dystonia and limb dystonias, myofacial pain, headache, bruxism, achalasia, trembling chin, spasticity, juvenile cerebral palsy, hyperhydrosis, excess salivation, non-dystonic tremors, cosmetic treatment of brow furrows, focal dystonias, spasticity, tension headache, migraine headache and lower back pain. Not infrequently, a significant amount of pain relief has also been experienced. These benefits have been observed after local intramuscular injection of, most commonly botulinum toxin type A, or one or another of the other botulinum neurotoxin serotypes.

The following list sets forth total (not per kg of patient weight) units of administrations of BOTOX® that have been used for therapeutic intramuscular injections. The list therefore provides guidelines for the unit amount of BOTOX® that can be used to denervate other, not listed, cholinergic muscles or muscle elements of similar size, such as cardiac muscle tissues and cardiac muscles elements. Thus, it is known that:

(1) about 75-125 units of BOTOX® per intramuscular injection (multiple muscles) can be used to effectively treat cervical dystonia;

(2) 5-10 units of BOTOX® per intramuscular injection can be used to effectively treat glabellar lines (brow furrows) (5 units injected intramuscularly into the procerus muscle and 10 units injected intramuscularly into each corrugator supercilii muscle);

(3) about 30-80 units of BOTOX® can be used to effectively treat constipation by intrasphincter injection of the puborectalis muscle;

(4) about 1-5 units per muscle of intramuscularly injected BOTOX® can be used to effectively treat blepharospasm by injecting the lateral pre-tarsal orbicularis oculi muscle of the upper lid and the lateral pre-tarsal orbicularis oculi of the lower lid.

(5) to treat strabismus, each extraocular muscle to be treated can be injected intramuscularly with between about 1-5 units of BOTOX®, the amount injected varying based upon both the size of the muscle to be injected and the extent of muscle paralysis desired (i.e. amount of diopter correction desired). A maximum dose per intramuscular injection should not exceed 25 U.

(6) to treat upper limb spasticity following stroke by intramuscular injections of BOTOX® into five different upper limb flexor muscles, as follows:
  (a) flexor digitorum profundus: 7.5 U to 30 U
  (b) flexor digitorum sublimus: 7.5 U to 30 U
  (c) flexor carpi ulnaris: 10 U to 40 U
  (d) flexor carpi radialis: 15 U to 60 U
  (e) biceps brachii: 50 U to 200 U. Each of the five indicated muscles can be injected at the same treatment session, so that the patient receives from 90 U to 360 U of upper limb flexor muscle BOTOX® by intramuscular injection at each treatment session.

Botulinum serotypes B, C1, E and F demonstrate a lower potency than BOTOX® and would therefore be used in greater amounts.

Botulinum toxin type A can be obtained by establishing and growing cultures of *Clostridium botulinum* in a fermenter and then harvesting and purifying the fermented mixture in accordance with known procedures. Botulinum toxin type A is available from several commercial sources, including Allergan, Inc., of Irvine, Calif. under the tradename BOTOX® Botulinum Toxin Type A purified complex and from Porton Products, Ltd., U.K. under the trade name DYSPORT.

Dickson, in J. Exper Med 37, 711-311 (1923) disclosed that the initial vagal nerves stimulation required to induce the physiological response of fewer heart beats per unit time was about eight times higher in botulinum intoxicated cats than it was in non-botulinum intoxicated cats.

All the botulinum serotypes are initially synthesized as inactive single chain proteins which must be cleaved or nicked by proteases to become neuroactive. The bacterial strains that make serotypes A and G possess endogenous proteases and these serotypes are therefore recovered from bacterial cultures predominantly in their active from. In contrast, types C1, D and E are synthesized by nonproteolytic strains and are therefore unactivated when recovered from culture. Serotypes B and F are produced by both proteolytic and nonproteolytic strains and may be recovered in either the active or inactive form. However, even the proteolytic strains that produce the type B serotype only cleave a portion of the toxin produced. The exact proportion of nicked to unnicked molecules depends on the length of incubation and the temperature of the culture. Therefore, a certain percentage of any preparation of type B toxin is likely to be inactive. The presence of inactive botulinum toxin molecules in a clinical preparation will contribute to the overall protein load of the preparation, which has been linked to increased antigenicity, without contributing to its clinical efficacy.

Although all botulinum toxins serotypes inhibit acetylcholine release at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type C1 has been shown to cleave both syntaxin and SNAP-25. These differences in mechanism of action may affect the relative potency and/or duration of action of the various botulinum toxin serotypes.

The size of an active botulinum toxin protein is determined by both the size of the neurotoxin molecule (150 kD for all serotypes) and its associated non-toxin proteins, which vary widely between serotypes. Type A is produced in both a 900 kD and a 500 kD form. Types B and C1 as a 500 kD complex only. Type D as both a 300 kD and 500 kD form. And types E and F as approximately 300 kD complexes only. Larger complexes contain hemaglutinin and a non-toxic nonhemaglutinin protein that improve the stability of the toxin molecule for oral absorption. It is possible that the larger complexes may have a slower rate of diffusion away from a site of injection.

Acetylcholine

Almost invariably, only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic and most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of the heart by the vagus nerves.

The efferent signals of the autonomic nervous system are transmitted to the body through either the sympathetic nervous system or the parasympathetic nervous system. The heart receives many sympathetic nerve fibers from the neck portion of the sympathetic chain. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Specific application of acetylcholine to the preganglionic sympathetic neurons which innervate the heart can result in tachycardia, as well as an increased force of contraction of the heart. Contrarily, specific application of acetylcholine to the preganglionic parasympathetic neurons which innervate the heart can result in bradycardia (as well as a decreased force of contraction of the heart, especially of the atria), the same bradycardiac result being obtained by application of acetyicholine to the postganglionic parasympathetic neurons which reside on or within cardiac muscle.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

What is needed therefore is a method for treating cardiac arrhythmia such as bradycardia and tachycardia without the numerous drawbacks and deficiencies of: (1) antiarrhythmic drug treatments, such as systemic effects, lack of specificity, and short duration of activity; (2) surgical, cryo or radiofrequency ablation, and; (3) which has a longevity of efficacy which can remove or significantly reduce the need for implantation of a pacemaker in order to substantially restore the heart's natural rhythm.

SUMMARY

The present invention meets this need and provides antiarrhythmic drug treatment methods for treating bradycardia and tachycardia without systemic effects, with specificity of drug action, with a relatively long duration of drug activity, without a need to carry out surgical, cryo or radiofrequency ablation, and with the longevity of drug efficacy by the disclosed methods permitting removal or significant reduction in the need for implantation of a pacemaker in order to substantially restore the heart's natural rhythm. Furthermore, methods within the scope of the present invention dramatically reduce the previously required daily antiarrhythmic drug administration frequency.

A preferred method within the scope of the present invention for treating a cardiac muscle disorder can be carried out by administering a neurotoxin to a patient suffering from a present or prospective cardiac muscle disorder. The cardiac muscle disorder can be a bradycardia or a tachycardia. In the case of a bradycardia, the administration step can be carried out by administration of the neurotoxin to or to the vicinity of a postganglionic parasympathetic neuron or by administration of the neurotoxin to or to the vicinity of a preganglionic parasympathetic neuron. In the case of a tachycardia, the administration step can be carried out by administration of the neurotoxin to or to the vicinity of a preganglionic sympathetic neuron.

Another preferred method within the scope of the present invention can be carried out by locally administering the neurotoxin to a cardiac muscle to treat the cardiac muscle disorder. Local administration of the neurotoxin to the desired cardiac muscle can be carried out by intrapericardial injection or infusion of the neurotoxin, by therapeutic cardiac catheterization or by direct intracardiac muscle injection of the neurotoxin.

Cardiac catheterization can be carried out by inserting a catheter which comprises a first end and a second end, and a hollow needle attached to the first end of the catheter into the circulatory system of a patient. Next the catheter is threaded within the circulatory system to the site of the cardiac muscle disorder. At this point, the hollow needle is inserted into the site of the cardiac muscle disorder. This is followed by injection of the selected neurotoxin into the cardiac muscle. Finally, the catheter is removed from the patient's circulatory system.

It is believed that the neurotoxin acts by inhibiting formation or release of a neurotransmitter, such as acetylcholine, from neurons in the vicinity of the cardiac muscle to be treated. Preferably, the neurotoxin is a botulinum toxin, such as botulinum toxin A which is locally administered to the cardiac muscle in an amount between about 0.01 U/kg and about 35 U/kg. More preferably, the botulinum toxin A is locally administered to the cardiac muscle in an amount of between about 0.1 U/kg to about 30 U/kg. Most preferably, the botulinum toxin A is locally administered to the cardiac muscle in an amount of between about 1 U/kg and about 25 U/kg.

A further preferred method within the scope of the present invention for treating a cardiac arrhythmia, such as a bradycardia, can comprise the steps of administration of a first antiarrhythmic drug, followed by administration of botulinum toxin. The first antiarrhythmic drug can be administered orally or parenterally. By parenteral administration it is meant that the first antiarrhythmic drug is not administered by either oral, intrapericardial or intracardiac routes of administration. By intracardiac administration it is meant, administration directly onto the surface of or into cardiac tissue, such as can be accomplished by, for example, therapeutic cardiac catheterization and by direct injection into cardiac muscle. In this method, the botulinum toxin can be administered intrapericardially or intracardially.

Preferably, the first antiarrhythmic drug is selected from the group consisting of atropine, amiodarone, sotalol, quinidine, procainamide, diiospyramide, lidocaine, mexiletine, flecainide, propafenone, beta blocking drugs, amiodarone, ibutilide and calcium blocking drugs with atropine and its salts and derivatives being a preferred first antiarrhythmic drug.

The botulinum toxin can be selected from the group consisting of botulinum serotypes, A, B, C1, D, E, F and G and preferably, the botulinum toxin is botulinum toxin type A.

A final preferred method within the scope of the present invention for treating a mammalian cardiac muscle disorder, such as bradycardia, can have the step of locally administering a therapeutically effective amount of a neurotoxin, such as botulinum toxin type A, to a cardiac muscle. Preferably, between about 10 U and about 300 U of the botulinum toxin type A is administered by the local administration step. More preferably, between about 20 U and about 200 U of the botulinum toxin type A is administered by the local administration step.

The site of cardiac muscle local administration, for treating bradycardia, is preferably the sinoatrial node and the local administration of the botulinum toxin type A can be carried out by either intrapericardial or by cardiac catheterization administration routes.

DESCRIPTION

The present invention is based upon the discovery that local administration of a neurotoxin to cardiac muscle can significantly alleviate cardiac muscle disorders, such as arrhythmia. Particular arrhythmias treatable by the present invention include bradycardia and tachycardia. By local administration it is meant that the neurotoxin is administered directly to, in, or to the vicinity of, the cardiac muscle to be treated. Local administration includes intrapericardial, intracardiac cardiac catheterization and direct cardiac muscle injection routes of administration for the neurotoxin. Peripheral muscle intramuscular, intrasphincter (i.e. in the GI tract), intraglandular, oral, transdermal and subcutaneous drug administration routes are unsuited for the practice of the present invention and are excluded from its scope.

I have discovered that a particular neurotoxin, botulinum toxin, can be used with dramatic ameliorative effect to treat both acute and chronic arrhythmia, significantly superceding thereby current antiarrhythmic drug therapy and additionally substantially removing the need to implant a pacemaker in a previously arrhythmic patient.

Thus, when atropine is ineffective and the patient has symptomatic bradycardia, vagal nerve inhibition and hence an increase in heart rate can be accomplished by administration of botulinum toxin to the heart, as for example in the vicinity of the SA node. Botulinum toxin administration can be accomplished by direct local injection to cardiac muscle, by cardiac catheterization or by intrapericardial injection or infusion. Significantly, a single administration injection of the botulinum toxin substantially reduces the symptoms of the bradycardia for from about two to about four months.

Administration of botulinum toxin according to the methods of the present invention can be used to treat and thereby reduce the occurrence of the symptoms of, inter alia, bradycardia induced acute myocardial ischemia or infarction, pulmonary embolism, embolic or hemorrhagic stroke, hyperalemia and conduction system disease. The resulting reduction of the incidence of bradyarrhythmia results directly in a decrease in the occurrence of cardiac arrest and ensuing sudden death.

Additionally, I have discovered that a neurotoxin such as a botulinum toxin can be used to treat bradycardia induced post surgical atrial fibrillation. Atrial fibrillation in the immediate post-operative period following cardiac surgery is a common clinical problem, occurring in 10-40% of patients. As with atrial fibrillation in any clinical setting, post-operative atrial fibrillation is associated with rapid ventricular response, congestive heart failure, and arterial embolization and stroke. Independent of these complications, post-operative atrial fibrillation is also an important cause of increased hospital length of stay and increased hospital costs in these patients.

The parasympathetic nerves (the vagi) are distributed mainly to the sinus (SA) and AV nodes, to a lesser extent to the muscle of the two atria and even less to the ventricular muscle.

Thus, for the treatment of bradycardia a preferred site of administration of the botulinum toxin is by local administration to ventricular muscle due to the presence of vagal nerves therein. A more preferred site of administration of the botulinum toxin for the treatment of bradycardia is by local administration to either or both of the muscles of the atria due to the greater distribution of parasympathetic nerve endings therein. A most preferred site of administration of the botulinum toxin for the treatment of bradycardia is by local administration to or to the vicinity of the SA and/or AV nodes because the most extensive distribution of parasympathetic nerve endings in cardiac muscles is at the indicated nodes.

When intrapericardial injection or infusion of a solution of botulinum toxin to the desired cardiac muscle location is carried out, needle guidance can be assisted by cardiac fluoroscopy or by more sensitive and specific imaging modalities such as magnetic resonance imaging and computed tomography.

The route of administration and amount of botulinum toxin administered can vary widely according to the particular cardiac muscle disorder being treated and various patient variables including size, weight, age, disease severity and responsiveness to therapy. Method for determining the appropriate route of administration and dosage are generally determined on a case by case basis by the attending physician. Such determinations are routine to one of ordinary skill in the art (see for example, *Harrison's Principles of Internal Medicine* (1997), edited by Anthony Fauci et al., 14th edition, published by McGraw Hill). For example, to treat bradycardia a solution of botulinum toxin is administered by intrapericardial injection to facilitate contact of the toxin with postganglionic parasympathetic nerve ending, while avoiding entry into the systemic circulation.

The specific dosage appropriate for administration is readily determined by one of ordinary skill in the art according to the factor discussed above. Additionally, the estimates for appropriate dosages in humans can be extrapolated from determinations of the amounts of botulinum required for effective denervation of other non-cardiac muscles. Thus, the amount of botulinum A to be injected is proportional to the mass of the cardiac muscle to be denervated. Generally, between about 0.01 and 30 units of a botulinum toxin per kg of total patient weight can be administered to effectively accomplish a toxin induced reversible postganglionic vagectomy upon administration of the neurotoxin at or to the vicinity of arrhythmic cardiac tissue. Less than about 0.01 U/kg of a botulinum toxin does not have a significant therapeutic effect, while more than about 30 U/kg of a botulinum toxin approaches the safety margin for a toxic dose. In exigent circumstances, up to about 35 U/kg of a botulinum toxin can be administered by local administration. Careful placement of the injection needle and a low volume of neurotoxin used prevents significant amounts of botulinum toxin from appearing systemically. A more preferred dose range is from about 0.1 U/kg to about 25 U/kg of a botulinum toxin. A most preferred dose range is from about 1 U/kg to about 20 U/kg of BOTOX®. The actual amount of U/kg of a botulinum toxin to be administered depends upon factors such as the extent (mass) of the arrhythmic tissue to be treated and the administration route chosen (i.e. by cardiac catheterization or by intrapericardial administration). Botulinum toxin type A is a preferred botulinum toxin serotype for use in the methods of the present invention.

I have found that the pericardial space can be safely and rapidly accessed for use as a drug delivery reservoir to which can be delivered a therapeutic dose of botulinum toxin for treatment of an arrhythmic heart. Thus, local cardiac drug delivery without system drug effect can be accomplished by accessing the normal pericardial space through the right atrial (transatrial therefore) appendage. Pericardial administration is a preferred method for administering botulinum toxin to the heart according to the present invention. For example, safe and rapid percutaneous subxyphoid access to the normal pericardium can be achieved using known methodologies. Additionally, also within the scope of the present invention is an iontophoretic transmyocardial method (as set forth in Circulation 85; 4; 1582-1593 (1992), the contents of which publication are incorporated herein in its entirety) adapted for local administration of a neurotoxin to cardiac muscle.

Another preferred method for local administration of botulinum toxin to the heart is by cardiac catheterization using a needle tip, infusion sleeve catheter, such as a drug delivery PTCA catheter. Alternatively, local intracardiac delivery of botulinum can be accomplished by use of a microporous balloon catheter or by use of a local adhesive (intracardiac) delivery technique.

Local, intracardiac catheter mediated delivery of a neurotoxin can be accomplished by use of a microporous infusion catheter (see e.g. Am Heart J. 1996 Nov.;132(5):969-72 and Cath & Cardiovasc Diagn 1997 Nov.;42(3):313-20) suitably modified to infuse the neurotoxin directly into the adjacent cardiac tissue at a relatively high pressure with minimal injury to the cardiac tissue. Other mechanisms for local intracardiac neurotoxin delivery include eluting stents, microspheres, neurotoxin-coated hydrogel (which can absorb hydrophilic drugs, such as botulinum toxin) balloon, iontophoretic devices and endocardiac paving and adhesive devices. The later method is carried out by catheter assisted lodging of a neurotoxin containing adhesive at or near a site of arrhythmic cardiac tissue (see e.g. Int J Artificial Organs 1997 Jun.;20(6):319-26).

Furthermore, the present invention also includes within its scope local administration of a neurotoxin to cardiac muscle by controlled release implants which are placed in direct contact with the pericardium, the epicardium or placed intracardially by catheterization. The neurotoxin is imbedded into or absorbed by the implant material prior to placement of the implant on or adjacent to a site of a cardiac muscle to be treated for a cardiac muscle disorder. Thus, the controlled release materials and procedure as set forth in J Cardio Pharm 24: 826-840 (1994) (the contents of which publication are incorporated herein in its entirety), can be adapted by one of ordinary skill in the art for local administration of a neurotoxin according to the present invention.

The pericardium is composed of an outer fibrous layer and an inner serous membrane with a single layer of mesothelial cells. The inner serous layer is attached to the surface of the heart and epicardial fat to form the visceral pericardium and this inner serous layer reflects back on itself to line the outer fibrous layer to form the parietal pericardium. Between these two layers lays the pericardial space, which is the only potential space in the normal pericardium. Favorable pharmacokinetic profiles have been obtained for basic fibroblast growth factor (bFGF) and nitroglycerin delivered into the pericardial space, using the pericardial space as a drug delivery reservoir for the delivery of therapeutic agents to the heart. See e.g. Cath & Cardiovasc Interv 1999; May;47(1):109-11.

Pericardial access is routinely performed to drain pericardial effusions as well as to administer drugs for the treatment of pericardial diseases such as malignant or infectious pericarditis. Access to the pericardial pace can be hindered by the difficulty of percutaneously entering the pericardial space in the absence of pericardial fluid. I have discovered that a therapeutically effective amount of an antiarrhythmic neurotoxin can be delivered to a normal (non fluid filled) percutaneously accessed pericardium. The method permits local intrapericardial delivery of a therapeutic dose of the neurotoxin delivery to arrhythmic cardiac tissues.

Botulinum toxin can also be used as a prophylactic agent to treat post-operative atrial fibrillation. To treat post operative arrhythmia, the botulinum toxin is locally administered 5-20 days before the surgery and again after surgery. The benefits of prophylactic therapy can include significant reductions in morbidity, hospital length of stay and overall costs. Botulinum toxin can also be used to treat angina.

EXAMPLES

The following examples provide those of ordinary skill in the art with specific preferred methods within the scope of the present invention for carrying out the present invention and are not intended to limit the scope of what the inventor regards as his invention.

For the practice of the methods set forth by Examples 1 and 2 below, the arrhythmic cardiac tissue to be injected with botulinum toxin is pinpointed by use of known electrophysiological means which, for example, can be used to generate a computer simulation of each heartbeat as it moves across the heart. Tracking of heart beats in this manner locate areas of the heart capable of producing arrhythmias and thereby identifies the sites or sites for therapeutic neurotoxin local administration as set forth herein.

Example 1

Therapeutic Cardiac Catheterization To Treat Arrhythmia

Intracardiac arrhythmic tissues can be treated by a method of the present invention using a variety of cardiac catheterization procedures, as exemplified below.

(a) Direct, injection of botulinum toxin to cardiac muscle can be carried out by an endomyocardial procedure where the biotome is replaced by a hollow needle through which a bolus injection of the toxin can be accomplished. Right ventricular injection can be accomplished by introducing a No. 7-9F catheter with a retractable sheathed needle via the right internal jugular vein using the usual Seldinger technique. The catheter is advanced under fluoroscopic guidance to the lateral wall of the right atrium. Using counterclockwise rotation, the catheter is advanced across the tricuspid valve and toward the interventricular septum. Position of the catheter against the interventricular septum is confirmed using 30 degrees right anterior oblique and 60 degree left anterior oblique fluoroscopic projections. Alternately, two dimensional echocardiography can be used to guide the position of the catheter. Contact with the myocardium is confirmed by the presence of premature ventricular contractions, lack of further advancement and transmission of ventricular impulse to the operator. The catheter sheath is then withdrawn to expose the needle tip. The catheter is readvanced to contact the myocardium and embed the needle therein. Secure lodgment of the needle tip within the myocardial wall is confirmed by fluoroscopy and by resistance to an operator applied slight withdrawal pressure (tugging) upon the catheter. 0.3 U/kg to 5 U/kg of BOTOX® are then injected into the myocardium and the catheter withdrawn. Right or left ventricular injection can also be accomplished from the femoral vein. The specific amount of BOTOX® administered by this intracardiac procedure depends upon a variety of factors to be weighed and considered within the discretion of the attending physician.

At the determined, localized site of arrhythmic cardiac tissue, botulinum toxin type A (available from Allergan, Inc., of Irvine, Calif. under the trade name BOTOX®) can be injected into the cardiac muscle through a 4 mm sclerotherapy needle passed through the infusion channel of the catheter and connected to a gravity driven device (overhead) or pump for infusion of the BOTOX® into the selected cardiac tissue.

(b) An alternate cardiac catheterization can be used to locate a recessed needle tipped catheter at the site of arrhythmia generating cardiac tissue. A thin flexible, hollow tube is inserted into the femoral artery in the groin. The catheter is then advanced under x-ray guidance (fluoroscopy) through the aorta to the particular cardiac tissue of interest. The purpose of cardiac catheterization is to inject the neurotoxin into the previously determined cardiac muscle. The patient should not eat or drink anything after midnight the day prior to the catheterization. A nurse will shave and wash the groin area to be inserted. The patient is hooked up to an EKG and a finger probe that will measure blood oxygen continuously.

A local anesthetic is applied to the groin area. The catheter is inserted and additional catheters can be inserted through the first one. The other catheters are pushed up though the aorta to the heart. Dye is injected and x-rays taken to ensure proper placement of the catheters.

Subsequent to BOTOX®, neurotoxin efficacy can be evaluated by the same means used to evaluate the effect of anti-arrhythmic drugs, such as by electrocardiogram (ECG).

Within seven days the bradycardia symptoms have substantially diminished and remain significantly alleviated for two to four months post injection. Insignificant amounts of the botulinum toxin appear systemically with no significant side effects.

Example 2

Intrapericardial Injection to Treat Arrhythmia (a) Intrapericardial injection of BOTOX® to treat an arrhythmia such as bradycardia is carried out by inserting a needle tip of a syringe through the unopened chest wall, and guided by fluoroscopy, through the thin fibrous baglike structure of the pericardium which surrounds the heart and into a pericardial sinus, preferably without contacting the heart itself.

A bolus injection of the botulinum toxin can be released into a sinus such as the transverse pericardial sinus adjacent to either the SA node or the AV node, at and in the vicinity of which the vagal nerves terminate on the heart. Preferably, the toxin is released at a location within the pericardium, under the endocardium, intermediate between the SA and AV nodes so as to maximum immediate toxin contact with vagal nerve termini.

(b) An alternative intrapericardial procedure for local cardiac drug delivery without system drug effect can also be accomplished by accessing the normal pericardial space through the right atrial appendage. The transatrial technique for accessing the pericardial space is as follows. An 8-F multipurpose guide is positioned under fluoroscopic guidance in the right atrial appendage. A custom fabricated 4-F catheter with a 21 gauge needle mounted at the tip is advanced through the guide, and a small perforation is made in the right atrial appendage. A soft 0.014 inch (0.036 cm) guide wire is advanced through the needle catheter and into the normal pericardial space. The guide wire confirms position in the pericardial space by conforming to the contour of the heart, secures the point of entry and allows over the wire exchanges of other catheters. The needle catheter is withdrawn over the wire and exchanged for a 4-F catheter with multiple side holes at its distal end, which is positioned and left in the pericardial space for delivery of neurotoxin. Radiopaque markers at the tip of all catheters improves visualization during fluoroscopy. Intrapericardial BOTOX® 0.3 U/kg to 5 U/kg is injected through the 4-F intrapericardial catheter without rapid diffusion into the systemic circulation.

(c) A further alternative procedure by which the pericardial space can be used as a drug delivery reservoir to deliver a therapeutic dose of BOTOX® to the heart is by subxyphoid access. A 6 Fr arterial catheter is femorally inserted for pressure monitoring. Safe and rapid percutaneous subxyphoid access to the normal pericardium is accomplished by gently advancing under fluoroscopic guidance an epidural introducer needle (Tuohy-17) with a continuous positive pressure of 20-30 mm Hg achieved by saline infusion using an intraflow system). The positive pressure is used to push the right ventricle (with a lower pressure) away from the needle's path. Entry to the pericardial space is suspected after an increase in the saline flow through the intraflow system. Access to the pericardial space is confirmed by the injection (intrapericardial) of 1 ml of diluted contrast under fluoroscopy. A soft floppy-tip 0.025" guidewire is then advanced to the pericardial space and the needle is exchanged for an infusion catheter. Between about 0.3 U/kg and about 5 U/kg of BOTOX® is injected.

(d) Alternatively, the arrhythmic tissue can be reached by endoscopy through the chest wall and pericardium using a standard forward viewing instrument or the site of the specific cardiac muscle area to be injected can be localized using known cardiac imaging methods.

Whether the catheterization or intrapericardial local administration routes are selected for the BOTOX®, the present methods present highly effective methods for treating a cardiac muscle disorder, such as bradycardia, by local administration of a therapeutically effective amount of the BOTOX® to the cardiac muscle.

The disclosed method can locally administer between about 10 U and about 300 U of the BOTOX® and preferably between about 20 U and about 200 U of the BOTOX® to or to the immediate vicinity of the cardiac muscle portion of the in vivo which generates or which assists in the generation of an acute or chronic episode of bradycardia. Thus, local administration of the BOTOX® to either or to both of the SA and AV nodes can be highly effective in the treatment of bradycardia. The specific unit amount of BOTOX® to locally administer depends upon a number of factors, as previously specified, including the age and health of the patient, the size of the patient's heart, the mass of arrhythmic cardiac tissue of the patient's heart to which the BOTOX® is to be locally administered, the local administration route and mechanism chosen, etc.

Example 3

Emergency Use of Botulinum Toxin

As a substitute or replacement for intravenous atropine, a patient experiencing acute bradycardia and imminent demise can be treated by immediate intraperitoneal injection of about 2 U/kg to about 35 U/kg of BOTOX®, without pericardial imaging assist. The injection is carried out by inserting the syringe (between the ribs and into the chest wall for a distance depending on the amount of adipose tissue present and the size of the patient's chest cavity) until lodgment of the needle tip into cardiac muscle has been achieved, as evidenced by vibratory movement of the syringe. Bolus injection of the botulinum toxin is then carried out. The time to antiarrhythmic effect of the botulinum toxin depends upon a number of factors, including the amount of BOTOX® locally administered.

A method for treating cardiac muscle disorders according to the invention disclosed herein has many advantages, including the following:

1. systemic drug presentation with its attendant side effects are avoided.

2. longevity of the effect of botulinum toxin obviates the need to implant a defibrillator or pacemaker.

Although the present invention has been described in detail with regard to certain preferred methods, other embodiments, versions, and modifications within the scope of the present invention are possible. For example, a number of the botulinum toxin serotypes administered to the postganglionic vagi nerve endings by various means can be used to treat a variety of cardiac muscle disorders. Additionally, other botulinum toxin serotypes, such as types B, C1, D, E, F and G can be used instead of and/or in conjunction with botulinum toxin type A.

Accordingly, the spirit and scope of the following claims should not be limited to the descriptions of the preferred embodiments set forth above.

I claim:

1. A method for treating a cardiac arrhythmia, the method comprising the step of administering a therapeutically effective amount of botulinum neurotoxin locally to the heart of a patient with a cardiac arrhythmia, wherein the botulinum neurotoxin reduces the occurrence of the symptoms associated with cardiac arrhythmia, thereby treating the cardiac arrhythmia.

2. The method of claim 1, wherein the botulinum neurotoxin is botulinum neurotoxin type A and the amount of botulinum neurotoxin type A administered to the heart is between about 0.01 U/kg and about 35 U/kg.

3. The method of claim 1, wherein the botulinum neurotoxin is botulinum neurotoxin type A and the amount of botulinum neurotoxin type A administered to the heart is between about 0.01 U/kg and about 30 U/kg.

4. The method of claim 1, wherein the botulinum neurotoxin is botulinum neurotoxin type A and the amount of botulinum neurotoxin type A administered to the heart is between about 1 U/kg and about 25 U/kg.

5. The method of claim 1, wherein the botulinum neurotoxin is selected from the group consisting of botulinum neurotoxins types, A, B, C1, D, E, F and G.

6. The method of claim 1, wherein the botulinum toxin is locally administered to cardiac muscle.

7. The method of claim 1, wherein the botulinum neurotoxin is intrapericardially injected to the patient.

8. The method of claim 1, wherein the administration comprises inserting a catheter into the circulatory system of the patient.

9. The method of claim 1, further comprising administering an antiarrhythmic drug other than the botulinum neurotoxin to the patient.

10. The method of claim 1, wherein the botulinum neurotoxin is botulinum neurotoxin type A, and the amount administered to the heart is between about 10 U and about 300 U of botulinum neurotoxin type A.

11. The method of claim 1, wherein the cardiac arrhythmia is tachycardia.

12. The method of claim 1, wherein the administration of the botulinum neurotoxin is effective in reducing the symptoms of the cardiac arrhythmia from about two months to about four months.

13. The method of claim 1, wherein the botulinum neurotoxin is administered to the pericardial space of the patient.

14. The method of claim 1, further comprising imaging a portion of the heart to assist with administration of the botulinum neurotoxin to the heart of the patient.

15. The method of claim 14, wherein the imaging comprises a fluoroscopic procedure.

16. A method for treating a cardiac arrhythmia, the method comprising the step of intracardiac injection of a therapeutically effective amount of botulinum neurotoxin type A to the heart of a patient with a cardiac arrhythmia, wherein the botulinum neurotoxin type A reduces the occurrence of the symptoms associated with cardiac arrhythmia, thereby treating the cardiac arrhythmia.

17. The method of claim 16, wherein the amount of the botulinum neurotoxin type A administered to the heart is between about 0.01 U/kg and about 35 U/kg.

18. The method of claim 16, wherein the administration of the botulinum neurotoxin type A is effective in reducing the symptoms of the cardiac arrhythmia from about two months to about four months.

* * * * *

UNITED STATES PATENT AND TRADEMARK OFFICE
CERTIFICATE OF CORRECTION

PATENT NO. : 7,485,624 B2
APPLICATION NO. : 11/236478
DATED : February 3, 2009
INVENTOR(S) : Stephen Donovan Page 1 of 1

It is certified that error appears in the above-identified patent and that said Letters Patent is hereby corrected as shown below:

Title Pg. Item (56) "Other Publications", delete "botulinal" and insert -- botulinum --, therefor.

Title Pg. Item (56) on page 2, under "Other Publications", delete "Botulinal" and insert -- Botulinum --, therefor.

Title Pg. Item (56) on page 2, under "Other Publications", line 6, delete "Botulinal" and insert -- Botulinum --, therefor.

In column 3, line 29, after "pacemaker" insert -- . --.

In column 3, line 53, after "entireties" insert -- . --.

In column 10, line 26-27, delete "acetyicholine" and insert -- acetylcholine --, therefor.

In column 11, line 56, delete "diiospyramide," and insert -- diisopyramide, --, therefor.

Signed and Sealed this

Twenty-first Day of April, 2009

JOHN DOLL
*Acting Director of the United States Patent and Trademark Office*